US00PP36806P2

(12) United States Plant Patent
Barr

(10) Patent No.: US PP36,806 P2
(45) Date of Patent: Jul. 8, 2025

(54) ***TAXODIUM* TREE NAMED 'Everbill'**

(50) Latin Name: *Taxodium distichum*
Varietal Denomination: Everbill

(71) Applicant: William C. Barr, Rosenberg, TX (US)

(72) Inventor: William C. Barr, Rosenberg, TX (US)

(73) Assignee: TREE SAP FARMS LLC, Houston, TX (US)

( * ) Notice: Subject to any disclaimer, the term of this patent is extended or adjusted under 35 U.S.C. 154(b) by 0 days.

(21) Appl. No.: 18/797,451

(22) Filed: Aug. 7, 2024

(51) Int. Cl.
*A01H 7/00* (2006.01)

(52) U.S. Cl.
USPC ..... Plt./213

(58) Field of Classification Search
USPC ..... Plt./213
CPC ..... A01H 7/00
See application file for complete search history.

(56) References Cited

U.S. PATENT DOCUMENTS

PP13,431 P2 * 12/2002 Berry ..... A01H 7/00
Plt./213

* cited by examiner

*Primary Examiner* — June Hwu
(74) *Attorney, Agent, or Firm* — Penny J. Aguirre

(57) ABSTRACT

A new cultivar of *Taxodium* tree named 'Everbill' that is characterized by its compact, upright, and narrow pyramidal growth habit with a central leader, its densely branched habit with branches that are held in a 45° angle to the trunk, its dark green immature and mature foliage, its growth rate of 91 cm per year with a 15-year-old mature trees reaching an average of 10 m in height and 3 m in width, and its lack of production of surface roots.

3 Drawing Sheets

Botanical classification: *Taxodium distichum.*
Varietal denomination: 'Everbill'.

BACKGROUND OF THE INVENTION

The present invention relates to a new and distinct cultivar of *Taxodium distichum* and will be referred to hereafter by its cultivar name, 'Everbill'. 'Everbill' represents a new bald cypress tree grown for landscape use.

The inventor discovered this new *Taxodium* as a whole plant mutation in January of 2018 at the Inventor's tree farm that had been planted with seedlings of *Taxodium distichum* in Rosenberg, Texas.

Asexual propagation of the new cultivar was first accomplished by the Inventor by softwood cuttings in July of 2018 in Glen Flora, Texas. Asexual propagation by softwood cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Everbill' as a unique cultivar of *Taxodium.*

1. 'Everbill' exhibits a compact, upright, and narrow pyramidal growth habit with a central leader.
2. 'Everbill' exhibits a densely branched habit with branches that are held in a 45° angle to the trunk.
3. 'Everbill' exhibits dark green immature and mature foliage.
4. 'Everbill' exhibits a growth rate of 91 cm per year, 15-year-old mature tree reaches an average of 10 m in height and 3 m in width.

5. 'Everbill' exhibits no production of surface roots.

Typical plants of *Taxodium distichum* differ from 'Everbill' in having a less dense plant habit, unpredictable growth rate and habit, a globose plant shape, and branching in various angles. 'Everbill' can be most closely compared to cultivars of *Taxodium distichum* 'Sofine' (U.S. Plant Pat. No. 13,431) and 'Peve Minaret' (not patented). 'Sofine' differs in having an open plant habit, less branching, different foliage colors; yellow-green immature foliage, lighter green mature foliage, orange-brown fall foliage, and a larger plant height and width. 'Peve Minaret' differs from 'Everbill' in having a more loosely arranged branching habit with a candelabra-like form.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website listing by Everde Growers.

BRIEF DESCRIPTION OF THE DRAWINGS

The accompanying color photographs illustrates the overall appearance and distinct characteristics of the new cultivar. The photographs were taken of 15-year-old tree as grown in the landscape in Glen Flora, Texas.

The photograph in FIG. 1 provides a side view of a tree of 'Everbill' in summer.

Figure 1:
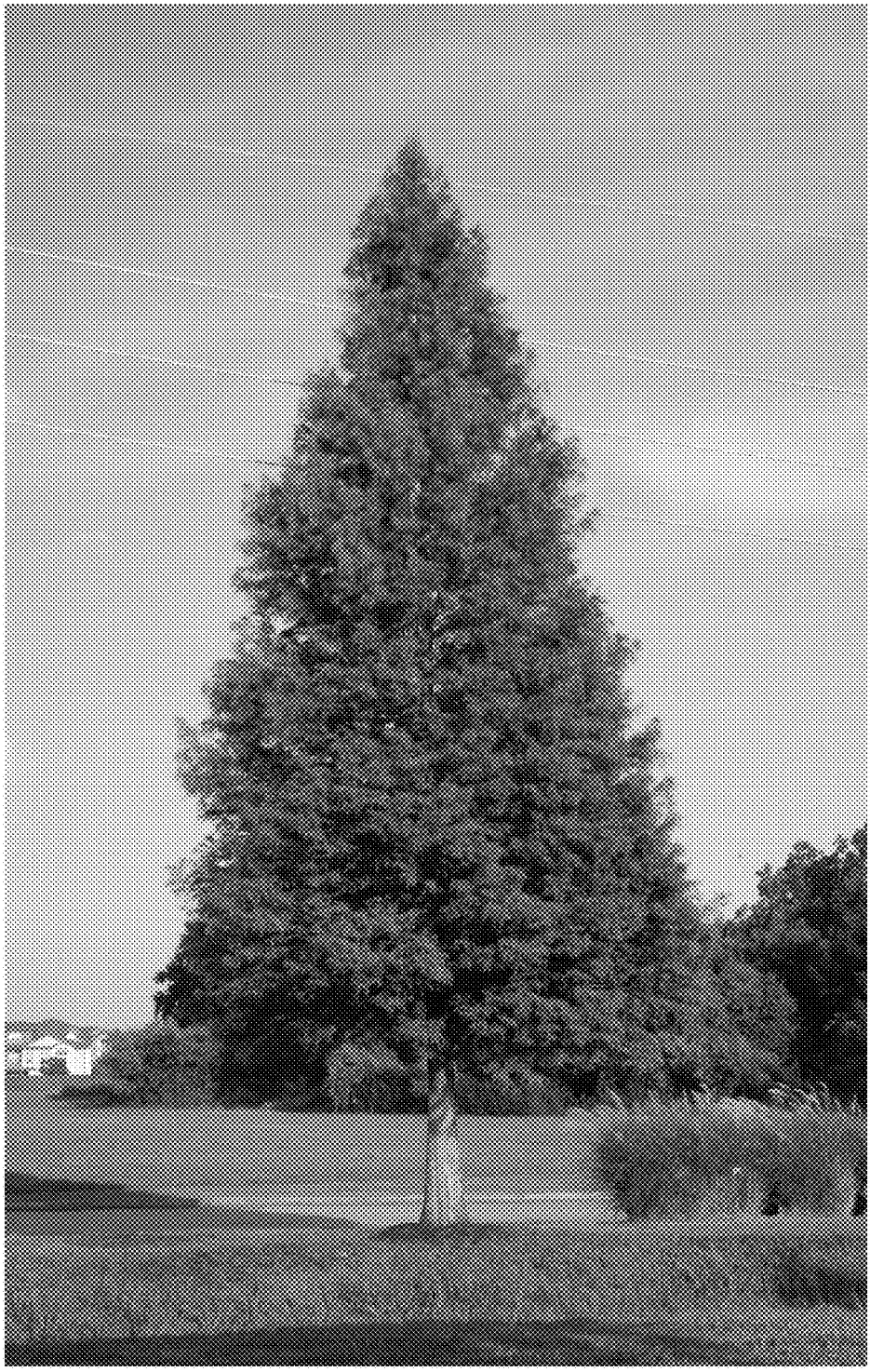
Figure 2:
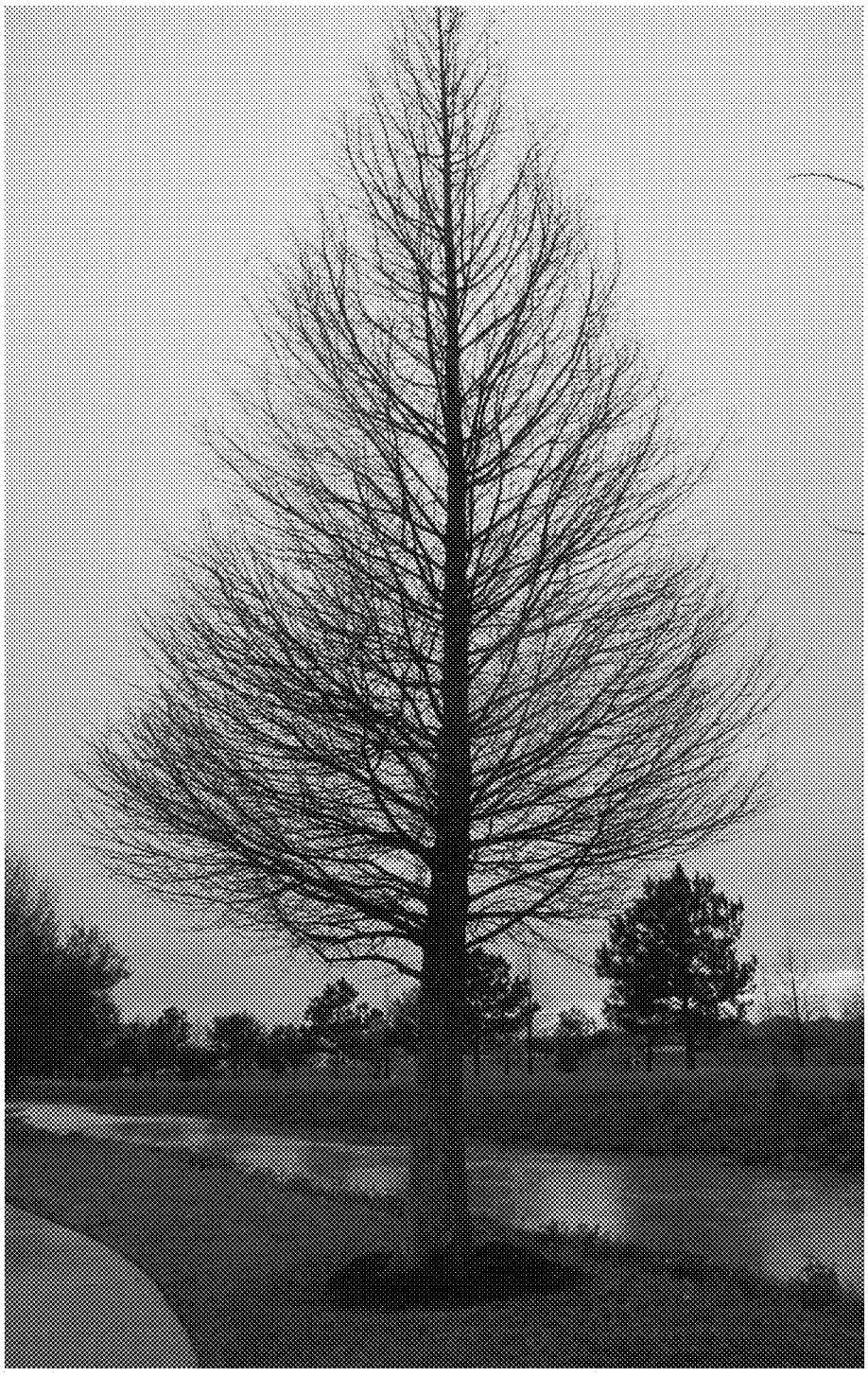

The photograph in FIG. 2 provides a side view of a tree of 'Everbill' when dormant.

Figure 3:
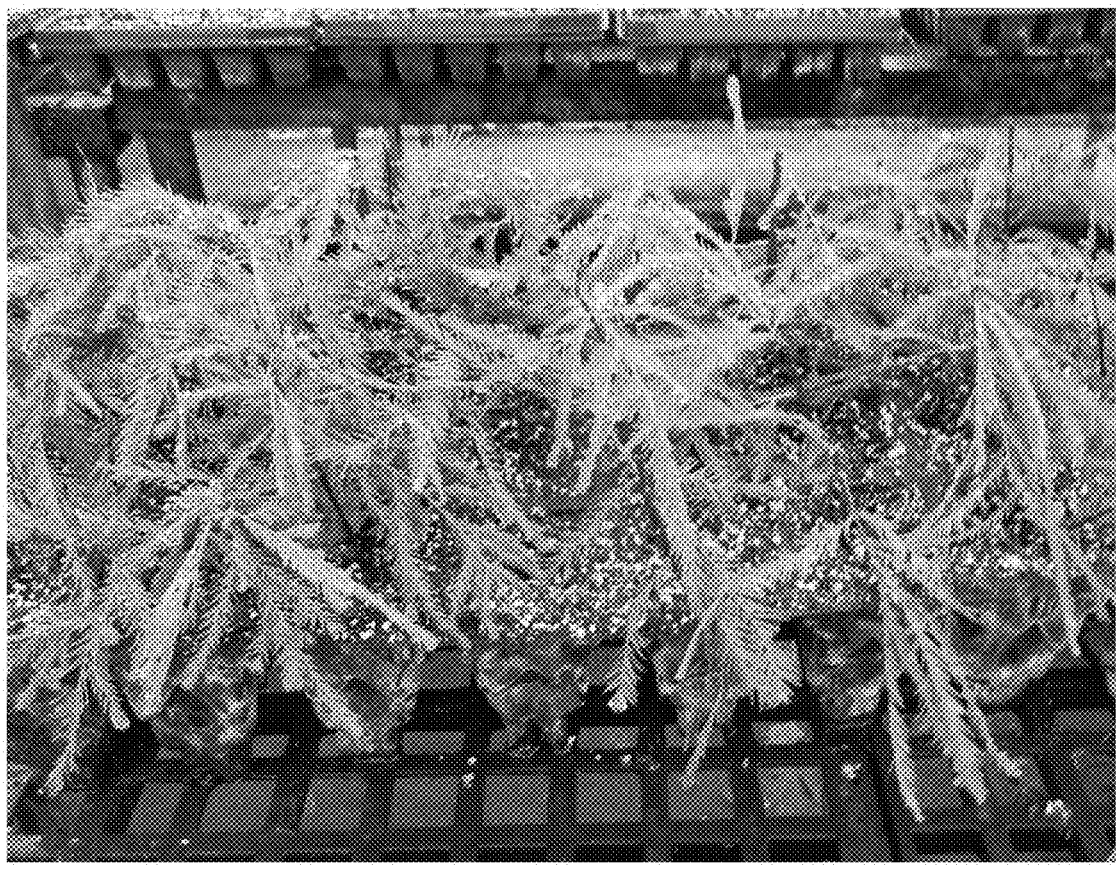

The photograph in FIG. 3 provides a close-up view of young trees of 'Everbill'.

The colors in the photographs may differ slightly from the color values cited in the detailed botanical description, which accurately describe the colors of the new *Taxodium*.

DETAILED BOTANICAL DESCRIPTION

The following is a detailed description of the new cultivar as observed on 15-year-old trees of 'Everbill' as grown outdoors in 30-gallon containers in Glen Flora, Texas and 3-year-old trees as grown outdoors in 2-gallon containers in Glen Flora, Texas. The phenotype of the new cultivar may vary with variations in environmental, climatic, and cultural conditions, as it has not been tested under all possible environmental conditions. The color determination is in accordance with The 2001 and 2015 Colour Charts of The Royal Horticultural Society, London, England, except where general color terms of ordinary dictionary significance are used.

General description:

*Plant type*.—Deciduous, coniferous tree.

*Growth habit*.—Dense, compact.

*Height and spread*.—Average of 1.3 m in height and 75 cm in width as a 3-year-old tree grown in a container, a 15-year-old mature tree in the ground reaches about 10 m in height and 3 m in width.

*Cold hardiness*.—At least in U.S.D.A. Zones 4 to 11.

*Diseases and pests*.—Observed to be disease free, however no susceptibility or resistance to specific diseases or pests is known.

*Propagation*.—Softwood cuttings.

*Root system*.—Moderate, freely branched, fleshy, no knees produced to date.

*Root development*.—Time required for root initiation is about 30 days, time required to produce to date a rooted young plant is about 9 months.

*Growth rate*.—Moderate, a average of 91 cm per year.

Branch description:

*Branch*.—Rounded.

*Branch size*.—Main branch; an average of 72 cm in length, 2.5 cm in diameter, lateral branches; an average of 65 cm in length, 7 mm in diameter.

*Branch surface*.—Young; glabrous, slightly glossy, sparsely covered with scales that are 1 mm in length, elliptical in shape, and match surface color, mature; glabrous and matte, lightly striated, older wood and bark; matte, exfoliating.

*Branch color*.—Young; a blend of N170A and N170C, mature; 174A to 174B, striations 200A, older wood and bark; 174A and 197A.

*Branching habit*.—Main branch; 1, lateral branches; average of 34 branches per main stem.

*Branch arrangement*.—Opposite, sometimes whorled.

*Branch aspect*.—Main branch; vertical, lateral branches; held horizontal (45° angle) from main and slightly bowed.

*Internode length*.—Average of 5 cm.

Foliage description:

*Lamina fragrance*.—Subtle cedar and pine scented when crushed or brushed.

*Lamina quantity*.—Average of 24 per lateral branch.

*Lamina aspect*.—Flat, feathery, arched downward to horizontal.

*Lamina arrangement*.—Alternate or opposite.

*Primary pinna*.—Oblong in shape, sessile attachment, average of 6.5 cm in length, 1.5 cm in width, 18 per lateral branch, held in opposite directions on the lateral branch, mid-rib 5 cm in length, 1.2 mm in diameter, glabrous, matte, and 138A in color.

*Secondary pinna*.—Linear in shape, veins are faintly linear, all vein surfaces and midrib match surface color, both surfaces glabrous, smooth, and matte, entire margins, cuneate base, average of 60 per primary pinna, apex is acute to bluntly acute, color; young upper and lower surface 136B, mature upper and lower surface 136B, fall; 167B to 167C.

Flower and fruit description: No flowers or fruit produced.

It is claimed:

1. A new and distinct cultivar of *Taxodium* tree named 'Everbill' as herein illustrated and described.

* * * * *